United States Patent [19]

Kötzsch et al.

[11] Patent Number: 4,924,021
[45] Date of Patent: May 8, 1990

[54] CYCLIC PHENOL ORGANOSILANES AND METHOD FOR THEIR PREPARATION

[75] Inventors: Hans-Joachim Kötzsch, Rheinfelden; Hans-Joachim Vahlensieck, Wehr, both of Fed. Rep. of Germany

[73] Assignee: Huels Aktiengesellschaft, Cologne, Fed. Rep. of Germany

[21] Appl. No.: 70,258

[22] Filed: Jul. 6, 1987

Related U.S. Application Data

[63] Continuation-in-part of Ser. No. 634,571, Jul. 26, 1984, abandoned.

[30] Foreign Application Priority Data

Aug. 2, 1983 [DE] Fed. Rep. of Germany ....... 3327795

[51] Int. Cl.$^5$ ................................................. C07F 7/08
[52] U.S. Cl. ..................................... 556/464; 556/486
[58] Field of Search ................................. 556/469, 486

[56] References Cited

U.S. PATENT DOCUMENTS 3,328,450  6/1967  Plueddemann ................. 556/464 X

FOREIGN PATENT DOCUMENTS 0415263  2/1974  U.S.S.R. ............................. 556/464
0480712  8/1975  U.S.S.R. ............................. 556/464

OTHER PUBLICATIONS

Bertrand et al., "Tetrahedron", 37, No. 14, pp. 2451 to 2466, 1981.

Primary Examiner—Paul F. Shaver
Attorney, Agent, or Firm—Felfe & Lynch

[57] ABSTRACT

Disclosed are 2-silacoumaranes and their o-allylphenolsilane monoester precursors and methods for their preparation. The benzene ring of these new compounds may be substituted with halogen and/or alkyl or alkyl halogen moieties. The cyclization of monoester precursor to the desired end products is performed in the presence of catalysts. This cyclization can be performed without the isolation of the o-allyphenolsilane monoester by feeding by the cyclization reactor with the starting products for the preparation of this intermediate directly after they have reacted, or, if trichlorosilane is the starting product, directly after they have been mixed.

Among other applications, the invention compounds are suitable for use as adhesion mediators and additives for coating compositions.

18 Claims, No Drawings

CYCLIC PHENOL ORGANOSILANES AND METHOD FOR THEIR PREPARATION

This application is a continuation in part of U.S. Ser. No. 06/634,571, filed Jul. 26, 1989, now abandoned.

BACKGROUND OF THE INVENTION

The subject matter of the invention is 2-silacoumaranes of the following formula

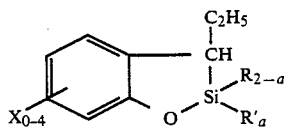

in which X represents halogen moieties and/or alkyl or fluorinated alkyl moieties of 1 to 4 carbon atoms, R' represents chlorine moieties or alkoxy moieties of 1 to 4 carbon atoms and R identical or different alkyl moieties of 1 to 4 carbon atoms; a represents 0 or 1 or 2.

Further subject matter of this invention is a method of preparing the claimed cyclic phenol organosilane esters by esterification of corresponding o-allyl phenols with hydrogen silanes of the general formula IV

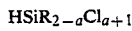

to form corresponding o-allyl phenolsilane monoesters of the general formula II

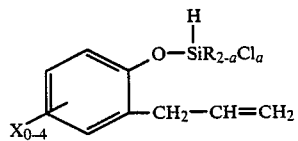

in which X, R and a have the meaning given above, for which patent protection is sought as new forms of matter, followed by cyclization of this allyl phenol silane monoester.

In German Pat. No. 22 37 961 chlorophenoxysilanes are described which have a bioresistant action which they retain even after incorporation into plastics. A disadvantage in these compounds is the vapor pressure of these compounds, which is too high for practical purposes and in some cases exceeds the maximum allowable concentrations.

The problem therefore existed of finding phenol organosilane compounds which have a bioresistant action and have a very low vapor pressure. Furthermore, the compounds sought are to have a maximum of four chlorine atoms on the phenol ring, and if possible they are to have the desired properties even if the aromatic ring is substituted with only two or three chlorine atoms.

THE INVENTION

As a solution to this problem, cyclic phenol organosilane esters have been found, of the formula

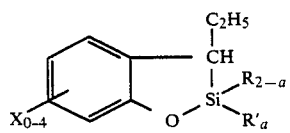

with a 2-silacoumarane structure, in which R represents alkyl moieties of 1 to 4 carbon atoms, R' represents halogen moieties or alkoxy moieties of 1 to 4 carbon atoms, and a can have, the values 0 or 1 or 2. X represents halogen moieties and/or alkyl or fluorinated alkyl moieties of 1 to 4 carbon atoms.

Furthermore, as a solution of this problem, as intermediates for these end products, o-allylphenolsilane monoesters have been found, of the formula

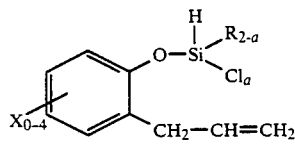

in which X, R, R' and a have the meaning given above.

It has not previously been possible to synthesize and characterize the claimed substances. All attempts to add hydrogen silanes (with hydrolyzable substituents on the silicon) onto o-allyl phenol have regularly failed to produce the distillable and definitely characterizable compounds of the above Structure I. Instead, they have resulted in nonvolatile or poorly volatile, unstable polymers of unclarified structure and complex composition (cf.: 1. K. A. Andrianov et al., Isv. Akad. USSR 1962, No. 11, p. 1953; 2. DAS 12 21 222, Examples 1 and 2).

For the synthesis and characterization it was therefore necessary for Andrianov, l.c., to use a complicated protective-group process with poor yields, which is not suitable for economical preparation, and also leads not to compounds of Structure I, but to the 7-ring structure postulated previously by other authors, namely 6,7-benzo-1-oxa-2-silepine. Attempts have therefore also been made by other authors to make available for the above-named applications the more easily accessible hydrosilation products of the allyl ether, e.g., of pentachlorophenol. The substance properties obtained by blocking the phenolic hydroxyl groups with an ether bond, however, are very different from the application properties according to the invention, of the claimed compounds.

In further solution of the above-named problem, a method has also been found for the preparation of allyl phenol silane monoesters of the above-given formula II and a method for the preparation of the new silacoumaranes.

The new allyl phenol silane monoesters of formula II are prepared from the corresponding o-allyl phenols of the general formula III:

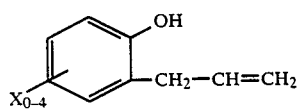

by reaction with hydrogen silanes, either using the hydrogen chlorosilane in excess or performing the reaction in the presence of acid-binding agents.

The use of an excess of hydrogen chlorosilanes is recommendable especially in the case of those chlorosilanes which are also able to form the corresponding diesters or triesters, such as trichlorosilane or methyl dichlorosilane, for example. The excess is then preferably to amount to between 2 and 5 moles of the silane. In the use of monochlorohydrogen silanes as starting product, such an excess is necessary only when acid-binding agents are not going to be used and the disadvantages associated therewith are acceptable.

In the practical preparation of o-allylphenoxychlorosilanes, when using an excess of silane, it is desirable to proceed by introducing o-allylphenol (or its kernel substitution products) into excess hydrogen chlorosilane and to use heat to drive out any hydrogen chloride that forms. The esterification itself, however, takes place in most cases at room temperature, so that, if desired, it is possible to operate also in this temperature range.

In the esterification of o-allyl phenols with monochlorohydrogen silanes, the esterification can optionally be performed in the presence of acid-binding substances, preferably amines or ammonia. The insoluble chloride thus produced is separated, and then the further processing or purification is performed by known methods.

The esterification of the allyl phenols can also be performed in the presence of a suitable solvent. This procedure is especially recommended when the allyl phenol used is a solid substance, such as for example the more highly halogenated allyl phenols and allyl methyl phenols.

The preparation of the cyclic phenol organosilane esters from the mono-o-allylphenoxysilanes is performed by catalytic hydrosilation, in which the carbon atom that is in position 2 of the allyl group reacts with the hydrogen atom of the hydrogen silyl moiety, i.e., but the silicon atom surprisingly adds on with hydrogen transposition in position 1 adjacent to the aromatic ring. Platinum or rhodium compounds, which can also be in the form of complex compounds, serve as catalysts, and inner cyclization takes place to form a ring of 5 ring atoms including the silicon and oxygen atom. The 7-ring structure (6,7-benzo-1-oxa-2-silepine) develops as a by-product by the addition of the silicon onto the terminal carbon atom of the allyl moiety. The 6-ring structure postulated by other authors, however, does not occur. This reaction is performed according to the invention in an inert diluent, at temperatures above 45° C. In practice, the o-allylphenoxysilane, dissolved in an inert solvent in some cases, is introduced into the stirred, liquid phase of an inert diluent containing the catalyst and maintained at temperatures above 45° C. The rather rapid cyclization reaction leads to the formation of monomeric rings, leading to the compounds of the above-named structure I, plus the corresponding 7-ring isomer. The percentage of the compounds of the particular structures varies, depending on the cyclization temperature, between 50 and 90% for structure I and 10 to 50% for the 7-ring isomer. The formation of the 7-ring isomer decreases with increasing reaction temperature.

It is a preferred embodiment of the process according to the invention to set out directly from the o-allyl phenols of the general formula III and $HSiR_{2-a}Cl_{a+1}$, not to isolate the mono-o-allylphenoxysilanes of structure II that form as intermediates, but only to produce them in situ as an intermediate product, and then immediately to perform the cyclization, and the esterification, if called for, of the cyclization product. This is accomplished by stirring the solution of the mono-o-allylphenoxysilane in excess $HSiR_{2-a}Cl_{a+1}$ prepared in the procedure described above and still containing inert solvent if desired, into the boiling diluent containing the catalyst, using a temperature at which any excess hydrogen chlorosilane will immediately distill off upon entry into the reaction solution. It is therefore advantageous in using this procedure to perform the cyclization reaction under a column which separates the emerging low-boiling components from any other substances that might be boiling with them.

It is furthermore an especially preferred embodiment of the method of the invention to perform the in situ production of the mono-o-allylphenoxysilanes of structure II in the line leading to the reactor of the cyclization reaction. In this line, the o-allyl phenol of formula III and $HSiR_{a-2}Cl_{a+1}$ are continuously premixed in a molar ratio of 1:2.5 to 5.0, and this mixture is delivered to the cyclization reactor. This procedure is especially suitable when trichlorosilane is used as one of the starting products.

In this embodiment, the catalyst can be put in after being dissolved by the component of general formula III, in the presence of inert solvents if desired, or it can additionally be contained in these inert solvents.

The compounds of the chlorosilane form according to structure I, in which R' represents halogen, prepared by the method according to the invention, can be used without further purification for different applications, such as glass fiber impregnation for example. They are also usable a adhesion mediating agents.

If the esterified form is desired, the chlorosilane form is immediately, without any other preliminary work-up, esterified by methods known in themselves, either by reacting it with alkyl orthoesters and distilling out the alkyl chloride and alkyl formiate that have formed, or the alcohol component is introduced in stoichiometric amount without contact with the gas phase of the reaction system, e.g., through a tube immersed in the liquid phase, operating preferably at an elevated reaction temperature up to the boiling point. If, after the hydrogen chloride has been driven out by heat, any acidity residues remain, they can be captured with acid-binding agents, such as amines and alcohols or alkyl orthoesters. If desired, the entire esterification can be performed in the presence of an acid-binding agent. The working up of the esterification product to the cyclic phenol organosilane esters of structure I, in which R' represents an alkoxy moiety, is performed according to commonly practiced methods such as filtration and vacuum distillation. The cyclic phenoxysilane bond surprisingly is not attached during these esterification operations.

Suitable starting substances of the general formula $HSiR_{2-a}CL_{a+1}$ are, for example, trichlorosilane, methyldichlorosilane, ethyldichlorosilane, propyldichlorosilane, isopropyldichlorosilane, n-butyldichlorosilane, isobutyldichlorosilane and dimethylchlorosilane. On the other hand, it appears that the hydrogen silane esters, corresponding to these chlorosilanes, with low aliphatic alcohols, such as for example trimethoxysilane etc., are not very well suited for the preparation of the cyclic phenol organosilane esters of the invention: in these alkoxysilanes the formation of the monoesters similar to general formula II takes place but incompletely, the products obtained are poorly defined, and the hydrosilation reaction starts only at substantially higher temperatures and gives only low yields of cyclization products.

Examples of suitable o-allyl phenols of general structural formula III are:
2-allyl-3.4.5.6-tetrachlorophenol,
2-allyl-3.4.6-trichlorophenol,
2-allyl-4.6-dichlorophenol,
2-allyl-4-chlorophenol,
2-allyl-6-chlorophenol,
2-allyl-3-methyl-4-chlorophenol,
2-allyl-5-methyl-4.6-dichlorophenol,
2-allyl-4-chloro-3.5-xylenol, 2-allyl-4.6-dichloro-3.5-xylenol,
2-allylphenol,
2-allyl-p-cresol,
2-allyl-5-methylphenol,
2-allyl-6-methylphenol,
2-allyl-4-isopropylphenol,
2-allyl-4-bromophenol,
2-allyl-3.5-dibromophenol,
2-allyl-4-fluorophenol,
2-allyl-4.6-difluorophenol,
2-allyl-3-fluoro-4-methylphenol,
2-allyl-5-trifluoromethylphenol,
2-allyl-4-trifluoromethylphenol,
2-allyl-3-trifluoromethylphenol, etc.

These o-allyl phenols are accessible in a simple and conventional manner by the Claissen transposition from the corresponding phenol allyl ethers at elevated temperature or in the cold in the presence of boron trichloride, it being necessary, of course, to take into account the different reactivities of the various phenols (cf. Houben-Weyl, Phenole I). For example, the transposition of phenol allyl ether requires 200° C. for about 10 hours, giving an approximately quantitative yield. On the other hand, 4-chloro-3,5-xylenol allyl ether reacts completely within 2 hours, and the 2-allyl-4-chloro-3,5-xylenol (MP 65° C.) can be isolated in an approximately quantitative yield only when the heat treatment is immediately stopped thereafter, on account of the threat of isomerization to the corresponding benzodihydrofuran (MP 36° C.). On the other hand, 2,4,5-trichlorophenol allyl ether is transposed above 150° C. in a very violent and highly exothermic reaction; this is mentioned especially for safety reasons.

Suitable catalysts in the cyclization reaction of the invention are among the compounds of metals of the 8th group of the periodic system, especially platinum and its compounds, e.g., in the form of platinum hydrochloric acid hexahydrate, platinum acetyl acetonate, the platinum-mesityl oxide complex etc., and rhodium, for example, in the form of rhodium-olefin, rhodium-silane, and rhodium-carboxylic acid complex compounds, in dilute to saturated solutions in, for example, alcohols, ketones, hydrocarbons and chlorinated hydrocarbons. The catalyst concentrations in accordance with the invention are between $10^{-2}$ and $10^{-8}$ millimole per mole of substrate.

Hydrocarbons and chlorinated hydrocarbons are suitable as cyclization media and as inert diluents and solvents for the starting components. It is advantageous to select the diluent used as the cylclization medium such that its boiling point determines the reaction temperature of the cyclization.

Substances suitable for this purpose are, for example, liquid aliphatic and aromatic hydrocarbons, such as hexane, isooctane, benzene, toluene, xylenes, Tetralin, and Decalins, chlorinated hydrocarbons such as, for example, trans-dichloroethylene, chloroform, carbon tetrachloride, trichloroethylene, perchloroethylene, 1,1,1-trichloroethane, trifluorotrichloroethane, chlorobenzene, and dichlorobenzenes.

When the inert solvent is used as the cyclization medium, the degree of dilution is preferably 100 to 500 ml of inert solvent, containing catalyst if desired, per mole of the substrate to be cyclized, and it is preheated to the cyclization temperature. Its use as solvent for the starting substance is important only if the corresponding crystalline or noncrystalline o-allyl phenol is thereby put into liquid form.

The aliphatic alcohols of one to four carbon atoms are used as esterification components, that is, methanol, ethanol, n-propanol, isopropanol, n-butanol, isobutanol, secondary butanol and tertiary butanol (the latter only in the presence of acid-binding amines or in the form of its alkali alcoholates). Also applicated are trialkyl orthoesters, e.g. trimethyl orthoformate, tributyl orthoformable etc.

For the neutralization or for use as acid-binding agents, any of the amines are suitable, such as for example ammonia, methylamine, dimethylamine, trimethylamine, triethylamine, pyridine etc., as well as the alcoholate forms of the esterification alcohols, or tri alkyl orthoesters, e.g. trimethyl orthoformable, triethyl orthoformable etc.

Substances of structure I prepared according to the method of the invention through monoesters of structure II, and containing as a rule 7-ring isomers, are, for example:

Si-Si-dialkoxy-3-ethyl-2-silacoumarane, containing Si-Si-dialkoxy-6,7-benzo-l-oxa-2-silepine from o-allylphenoxydichlorosilane;

Si-alkoxy-Si-methyl-3-ethyl-2-silacoumarane from (o-allylphenoxy)-methylchlorosilane;

Si-Si-4,6-tetramethyl-3-ethyl-5-chloro-2-silacoumarane from dimethyl(2-allyl-4-chloro-3,5-xylenoxy)silane;

Si-Si-dialkoxy-3-ethyl-4,6-dimethyl-5-chloro-2-silacoumarane from 2-allyl-4-chloro-3,5-xylenoxydichlorosilane;

Si-Si-5,7-tetramethyl-3-ethyl-4,6-dichloro-2-silacoumarane from dimethyl(2-allyl-3,5-dimethyl-4,6-dichlorophenoxy)-silane;

Si-methyl-Si-alkoxy-3-ethyl-5-isopropyl-2-silacoumarane from methyl-2-allyl-4-isopropylphenoxychlorosilane;

Si-Si-dialkoxy-3-ethyl-6-trifluoromethyl-2-silacoumarane from 2-allyl-5-trifluoromethylphenoxydichlorosilane, the corresponding Si-methyl-5-trifluoromethyl derivative of methyl(2-allyl-4-trifluoromethylphenoxy)chlorosilane and its corresponding Si-Si-dimethyl derivative of dimethyl(2-allyl-5-trifluoromethylphenoxy)-silane;

Si-Si-dialkoxy-3-ethyl-4,5,7-trichloro-2-silacoumarane from 2-allyl-3,4,6-trichlorophenoxydichlorosilane.

The substances of the claimed structure I and their 7-ring isomers, prepared according to the invention, have good adhesive and crosslinking properties for phenolic resin-crosslinking epoxy resins containing fillers, especially when they have no additional or only one additional alkyl substituent in the aromatic part. When they are used for the sealing of electronic components they have good stability of adhesion, low moisture diffusion and high electrical resistance, thereby providing improved protection of these components against corrosion. For this purpose are concentrations of 0.2 to 2 wt. % of the structure I substances adapted to the resins applicable.

The substances of the claimed structure I prepared according to the invention, especially when they bear substituents in the aromatic part, also have very broad activities, or even activities graded according to their substitution, for example against gram positive and gram negative bacteria and yeast fungi, and repellent actions against plant life and insects. The claimed use includes the preservative and/or sterilizing and/or bioresistant treatment of materials, e.g., the preservation of fabrics, paper and wood, the sterilizing treatment of ceramic surfaces, the insect pest-repellent treatment of natural substances, plastics, and especially electrical insulating materials, the antifouling treatment of boats and underwater construction etc. Especially advantageous is the strength of adherence which these phenol organosilanes develop by means of their silane component. The silane component fixes the phenol component by means of its known adhesive property. In this manner, longer-lasting effects are achieved in the claimed applications. The adhesion can be further increased according to the invention by mixing the phenol organosilanes in their application together with amino organosilanes, as for example with 3-aminopropyltriethoxysilane or 3-N,N-dimethylaminopropyltrimethoxysilane. At the same time, a remarkable enhancement of their effectiveness against yeast fungi and algae is achieved by this measure in accordance with the invention.

This further improvement of the effectiveness of the phenol organosilanes against yeas fungi and algae is achieved in accordance with the invention also by combining them with amines such as abietic amine for example.

EXAMPLES

The following examples will explain the invention, without, however, limiting it:

EXAMPLE 1

(a) In a 4-liter flask equipped with reflux condenser, stirrer and heater and a bottom drain valve, 2710 g (20 mol) of trichlorosilane was heated at ebullition and then 671 g (5 mol) of o-allylphenol was fed into it from a dropping funnel through a submerged introduction tube, with stirring, over a period of about 80 minutes, while the HCl that formed was completely boiled away.

The gas chromatogram of the fully reacted mixture indicated an approximately 25% solution of o-allylphenoxydichlorosilane, which is isolated in a virtually quantitative yield from a parallel attachment. BP/1 78° C.

| Elemental analysis (calculated for $C_9H_{10}Cl_2OSi$, M. 233): | | | |
|---|---|---|---|
| C | H | Cl | Si |
| Calculated 46.34% | 4.36% | 30.44% | 12.04% |
| Found 46.10% | 4.58% | 30.62% | 11.83% |

(b) In a heated 4-liter flask with magnetic stirrer, internal thermometer and a 20-tray column with an automatic column head, 1 liter of trichlorethylene was heated to ebullition. After the addition of 0.5 ml of an 0.01 molar solution of hexachloroplatinic acid hexahydrate in acetone, with stirring, the raw solution obtained under (a) was introduced through a submerged tube over a period of 120 minutes, the trichlorosilane distilling off at a rate controlled by the feed of the raw solution, and the boiling temperature increased from about 82° C. to about 96° C. Boiling was continued for 30 minutes thereafter.

The gas chromatogram indicated an approximately 46% solution of an approximately 5 : 2 mixture of Si-Si-dichloro-3-ethyl-2-silacoumarane with its Si-Si-dichloro-6,7 -benzo-1-oxa-2-silepine isomer which was isolated by distillation from a parallel attachment in a 94.5% yield. BP/1 74-76° C.

| Elemental analysis (calculated for $C_9H_{10}Cl_2OSi$, M. 233): | | | |
|---|---|---|---|
| C | H | Cl | Si |
| Calculated 46.34% | 4.36% | 30.44% | 12.04% |
| Found 46.41% | 4.65% | 30.70% | 11.75% |

(c) An excess (1600 g = 15 mol) of trimethylorthoformiate was metered into the boiling raw solution according to (b) over a period of 140 minutes (slowly at first, then more rapidly after about 60% had been added), while methyl chloride escaped through the top of the column and methyl formiate (BP 31° C.) was distilled out, the boiling temperature of the reaction mixture rising to 104° C. After that, boiling was continued for 16 hours, and the product was worked up by distillation.

Vacuum distillation through a Sulzer BX packing with 8 trays delivered 1032 g (92%) of an approximately 5 : 2 mixture of Si-Si-dimethoxy-3-ethyl-2-silacoumarane with its Si-Si-dimethoxy-6,7-benzo-1-oxa-2-silepine isomers. BP/1 95°-96° C.; $D_4^{20}$ 20 1.1168.

| Elemental analysis (calculated for $C_{11}H_{16}O_3Si$, M. 224.3): | | |
|---|---|---|
| C | H | Si |
| Calculated 58.89% | 7.19% | 12.52% |
| Found 58.60% | 7.29% | 12.30% |

The NMR spectrum indicates:

73% of the structure O—Ph—CH(Et)—Si(OMe)$_2$ and

27% of the structure O—Ph—(CH$_2$)$_3$Si(OMe)$_2$.

EXAMPLE 2

(a) Similarly to Example 1, part (a), 1151 g (10 mol) of methyldichlorosilane was reacted with 671 g (5 mol) of o-allylphenol while the boiling temperature rose to 47° C.

From a parallel attachment 1204 g of allylphenoxymethylchlorosilane BP/2 73° C. was isolated by distillation.

| Elemental analysis (calculated for $C_{10}H_{13}ClOSi$, M. 213): | | | |
|---|---|---|---|
| C | H | Cl | Si |
| Calculated 56.6% | 6.2% | 16.5% | 13.2% |
| Found 56.4% | 6.5% | 16.7% | 12.9% |

(b) Similarly to Example 1, part (b), a raw solution according to part (a) was cyclized in one liter of boiling toluene using 0.5 ml of an 0.01-molar solution of the platinum mesityl oxide complex in acetone as catalyst. The distillative work-up yielded 1012 g of an approximately 3 : 1 mixture of Si-methyl-Si-chloro-3-ethyl-2-silacoumarane with its Si-methyl-Si-chloro-6,7-benzo-1-oxa-2-silepine isomers. BP/2 68 to 69° C.

| Elemental analysis (calculated for $C_{10}H_{13}ClOSi$, M. 213): | | | |
|---|---|---|---|
| C | H | Cl | Si |
| Calculated 56.6% | 6.2% | 16.5% | 13.2% |
| Found 56.3% | 6.4% | 16.5% | 13.0%. |

(c) Similarly to Example 1, part (c), 650 g of excess trimethylorthoformiate was gradually added to a boiling raw solution according to part (b) within 70 minutes.

The distillative work-up yielded 987 g of an approximately 3:1 mixture of Si-methyl-Si-methoxy-3-ethyl-2-silacoumarane with its Si-methyl-Si-methoxy-6,7-benzo-1-oxa-2-silepine isomers.

BP/2 93° C.; $D_4^{20}$ 1.060.

Elemental analysis (calculated for $C_{11}H_{16}O_2Si$, M. 208.3):

|  | C | H | Si |
|---|---|---|---|
| Calculated | 63.4% | 7.7% | 13.5% |
| Found | 63.3% | 7.9% | 13.2% |

The NMR spectrum indicates

75% of the structure O—Ph—CHEt—SiMe(OMe) and
                     |_____|

25% of the structure O—Ph—(CH$_2$)$_3$SiMe(OMe).
                     |_____|

EXAMPLE 3

(a) In a 4-liter flask equipped for heating and stirring and with a reflux condenser and bottom drain valve, 813 g (6 mol) of trichlorosilane was heated to ebullition and then, through an immersed tube, the solution of 590 g (3 mol) of 2-allyl-3,5-dimethyl-4-chlorophenol in 880 ml of dichloromethane was fed from a dropping funnel, with stirring, within about 80 minutes, while the hydrogen chloride that formed was boiled out completely.

From a parallel attachment, 2-allyl-3,5-dimethyl-4-chlorophenoxy-dichlorosilane was isolated by distillation in a virtually quantitative yield. BP/0.5 115° C.

Elemental analysis (calculated for $C_{11}H_{13}Cl_3OSi$, M. 295.7):

|  | C | H | Cl | Si |
|---|---|---|---|---|
| Calculated | 44.68% | 4.43% | 35.98% | 9.50% |
| Found | 44.41% | 4.72% | 36.20% | 9.25% |

(b) Similarly to Example 1, part (b), the raw solution obtained under a) was metered into one liter of boiling toluene which contained 0.4 ml of an 0.01-molar solution of $H_2PtCl_6 \cdot 6H_2O$ in isopropanol, while the trichlorosilane and the dichloromethane distilled off at a rate controlled by the rate of the raw feed, and the boiling temperature rose from 110° C. to about 119° C. Boiling was continued for 20 minutes.

An approximately 2 : 1 mixture of Si-Si-dichloro-3-ethyl-4,6-dimethyl-5-chloro-2-silacoumarane with its Si-Si-dichloro-6,7-(6,8-dimethyl-7-chlorobenzo)-1-oxa-2-silepine isomers was isolated by distillation from a parallel attachment in a 92% yield. BP/0.5 112 to 114° C.

(c) The raw solution from part b) was adjusted to 44° C., and then 128 g (4 mol) of methanol was fed in over a period of 30 minutes through a feed tube immersed in the reaction solution, while hydrogen chloride evolved. Then the mixture was heated within about 20 minutes to about 100° C. and thus the hydrogen chloride was driven out by heat (finally in a vacuum at about 140 mbar). Then an additional 64 g (2 mol) of methanol was added to the mixture at about 70° C. and neutralized with about 100 g of ammonia. After filtration in the cold, 758 g (88%) of an approximately 2 : 1 mixture of Si-Si-dimethoxy-3-ethyl-4,6-dimethyl-5-chloro-2-silacoumarane with its Si-Si-dimethoxy-6,7-(6,8-dimethyl-7-chloro- benzo)-1-oxa-2-silepine isomers was isolated by vacuum distillation. BP/0.5 127 to 129° C.; $D_4^{20}$ 4 1.1177.

Elemental analysis (calculated for $C_{13}H_{19}ClO_3Si$, M. 286.8):

|  | C | H | Cl | Si |
|---|---|---|---|---|
| Calculated | 54.43% | 6.68% | 12.36% | 9.79% |
| Found | 54.25% | 6.60% | 12.50% | 9.81%. |

EXAMPLE 4

Similarly to Example 3, (a) 607 g (3 mol) of 2-allyl-5-trifluoromethylphenol as a solution in 600 ml of perchlorethylene was reacted with 1626 g (12 mol) of trichlorosilane to form 2-allyl-5-trifluoromethylphenoxydichlorosilane. BP/1 103 to 105° C.

Elemental analysis (calculated for $C_{10}H_9Cl_2F_3SiO$, M. 301.176):

|  | C | H | Cl | F | Si |
|---|---|---|---|---|---|
| Calculated | 39.87% | 3.01% | 23.55% | 18.93% | 9.33% |
| Found | 39.80% | 3.22% | 23.30% | 19.05% | 9.08% |

(b) A raw solution from (a) was cyclized similarly in 500 ml of boiling perchlorethylene with distillation of the excess trichlorosilane and a temperature increasing from 124° C. to about 128° C., to form an approximately 3 : 2 mixture of Si- Si-dichloro-3-ethyl-6-trifluoromethyl-2-silacoumarane with its Si-Si-dichloro-6,7-(8-trifluoromethylbenzo)-1-oxa-2-silepine isomers. BP/1 104 to 106° C.

Elemental analysis (calculated for $C_{10}H_9Cl_2F_3SiO$, M. 301.176):

|  | C | H | Cl | F | Si |
|---|---|---|---|---|---|
| Calculated | 39.87% | 3.01% | 23.55% | 18.93% | 9.33% |
| Found | 39.61% | 3.30% | 23.25% | 18.85% | 9.04% |

(c) A raw solution from (b) was esterified similarly to Example 1 with 900 g (about 6 mol) of triethylorthoformiate and worked up to the approximately 3 : 2 mixture of Si-Si-diethoxy-3-ethyl- -trifluoromethyl-2-silacoumarane with its 7-ring isomers in a yield of 903 g (94.0%). BP/0.5 128° to 130° C., $D_4^{20}$ 1.1241.

Elemental analysis (calculated for $C_{14}H_{19}F_3O_3Si$, M. 320.4):

|  | C | H | F | Si |
|---|---|---|---|---|
| Calculated | 52.48% | 5.98% | 17.79% | 8.77% |
| Found | 52.20% | 6.05% | 17.80% | 8.50% |

EXAMPLE 5

In a 6-liter flask equipped with heating, with a magnetic stirrer, an internal thermometer, a 20-tray column (with automatic head and a gas duct to an HCl washer)

and a 1-liter and a 2-liter dropping funnel whose stems are combined in a Y and carried through a trap line filled with a number of 4-millimeter porcelain saddles and carried in the introduction tube into the gas phase of the reaction flask, one liter of trichlorethylene was heated to ebullition. After the addition of 0.3 ml of an 0.01-molar solution of $H_2PtCl_6 \cdot 6H_2O$ in acetone, o-allylphenol was fed into the reactor from the one-liter funnel, and methyldichlorosilane was fed simultaneously from the 2-liter funnel, in a molar ratio of about 1 : 2.5, in amounts totaling 1075 g (8 mol) of o-allylphenol and 2300 g (20 mol) of methyl hydrogen dichlorosilane, over a period of 140 minutes, at a uniform rate of feed. With constant stirring and immediate distillation of hydrogen chloride and the excess methyldichlorosilane, the reaction temperature rose from about 82° C. to about 97° C. Boiling was continued for about 1 hour after the addition of the components had ended.

An approximately 3:2 mixture of Si-methyl-Si-chloro-3-ethyl-2-silacoumarane and its 7-ring isomers was isolated by distillation in an approximate 95% yield. BP/1 72 to 75° C.

Elemental analysis (calculated for $C_{10}H_{13}ClOSi$, M. 212.75):

|  | C | H | Cl | Si |
|---|---|---|---|---|
| Calculated | 56.45% | 6.16% | 16.67% | 13.20% |
| Found | 56.58% | 6.44% | 16.50% | 12.90%. |

Ethyl ester: By esterification with ethanol and $NH_3$. BP/1 95 to 97° C.; $D_4^{20}$ 1.1187.

Elemental analysis (calculated for $C_{12}H_{18}O_2Si$, M. 222.4):

|  | C | H | Si |
|---|---|---|---|
| Calculated | 64.82% | 8.16% | 12.63% |
| Found | 65.0% | 8.2% | 12.4%. |

EXAMPLE 6

In a 4-liter flask equipped with heating and a stirrer, and with a reflux condenser and a dropping funnel, about 80 g of ammonia in excess was introduced into the solution of 544 g (2 mol) of 2-allyl-3,4,5,6-tetrachlorophenol and 190 g (2 mol) of hydrogen dimethylchlorosilane in 1600 ml of anhydrous toluene, with stirring, at room temperature, whereupon a white precipitation of ammonium chloride took place. Then the temperature was raised within 1 hour to the boiling temperature of the reaction mixture and boiling continued for about 20 minutes. The mixture was filtered cold. By distillative work-up, 622 g (94%) of hydrogen dimethyl-(2-allyl-3,4,5,6-tetra-chlorophenoxy)-silane was isolated.

BP/1 152 to 154° C.

Elemental analysis (calculated for $C_{11}H_{12}Cl_4OSi$, M. 330):

|  | C | H | Cl | Si |
|---|---|---|---|---|
| Calculated | 40.02% | 3.66% | 42.96% | 8.51% |
| Found | 39.70% | 3.50% | 42.70% | 8.24% |

660 g (2 mol) of this hydrogen dimethyl-(2-allyl-3,4,5,6-tetrachlorophenoxy)-silane, dissolved in 330 ml of toluene was fed uniformly for 40 minutes in 600 ml of boiling toluene containing 0.5 ml of catalyst solution (as in Example 1). Then boiling was continued for 2 hours. By distillative work-up, 587 g (about 89%) of Si-Si-dimethyl-3-ethyl-4,5,6,7-tetrachloro-2-silacoumarane was isolated in an approximately 3 : 2 mixture with 7-ring isomers.

BP/0.5 152 to 156° C.

Elemental analysis (calculated for $C_{11}H_{12}Cl_4OSi$, M. 330):

|  | C | H | Cl | Si |
|---|---|---|---|---|
| Calculated | 40.02% | 3.66% | 42.96% | 8.51% |
| Found | 39.80% | 3.80% | 42.69% | 8.25% |

EXAMPLE 7

Effectiveness Against Filamentous Algae 0.5 weight-percent of an equimolar mixture of 3-N,N-dimethylaminopropyltrimethoxysilane and the Si-Si-dimethyl-3- ethyl-4,5,6,7-tetrachloro-2-silacoumarane with a content of 7-ring isomer, prepared in Example 6, was added in a 40% solution in ethanol to a commercial anticorrosive varnish based on ethylpolysilicate 40 and zinc dust. The varnish thus treated was applied to 200 ×40 mm sheet steel test strips and cured. Test strips which were not coated with treated varnish served for comparison. The test organisms were mainly cultures of green algae containing mainly Oedogonium and Spyrogyra. After about 3 months of standing, the control strips were coated with algae, while the treated test strips showed no growth of algae.

EXAMPLE 8

Long-Term Test

Strips of a desized nonwoven glass fiber material 4 cm long and 0.5 cm wide were impregnated by immersing them and drying them at 120° C. in a 70% aqueous acetone solution, adjusted to pH 4 with a few drops of acetic acid, of 2 weight-percent of the mixture of 4-chloro-3,5-xylenol organosilane and isomers prepared in Example 3.

The bacteriological testing was performed on Bacterium subtilis and the fungus testing on Candida albicans. For the purpose of the test, the sample strips were let stand in sterile Petri dishes for 2 days. After testing for sterility, the strips were each immersed for 15 minutes in 15 ml of the culture suspension or solution, blotted with a sterile pad, set aside in sterile Petri dishes, transferred about one day later to 10 ml of nutrient solution, and observed for growth. Some of the test strips were put away sealed in Petri dishes as controls. The rest of the test strips were let stand in a current of fresh air whose temperature and relative humidity varied in a regular manner daily between 16 hours at 40° C. and 50% relative humidity, and 8 hours at 20° C. and 70% relative humidity, for the purpose of exposure to alternating climates.

The experiment showed that the test strips exposed to the alternating climate had retained their bactericidal and fungicidal properties and showed no appreciable difference in the result, in contrast to the controls. In the final test they both showed no bacterial growth.

EXAMPLE 9

A mixture of 30 g Scadoform L 9(novolak resin; Arches Daniels) 50 g Aralolit 7097, 20 g Araldit 6071 (both epoxy resins; ClBA), and 3g of 3-ethyl-2.2-dimethoxy-2- silacoumarane in 100 μl of toluene was precondensed for 60 minutes at 112° C. The resulting viscous compound was homogenized with 9 g of pine oil, 3 g of 2-nonylpipendines and 250 g Cabone N70-T5 ( fumed silica; cabot), applied as a coating for silicon-wafers, and curved for 2 hours at 200° C. The finished coating showed a bending strength of 20–2 kp/mm$^2$ and a volume resistivity of $5.4–10^{16}$ Ohm. cm. The wafer sorphon was lower than 0.1%.

It will be understood that the specification and examples are illustrative but not limitative of the present invention and that other embodiments within the spirit and scope of the invention will suggest themselves to those skilled in the art.

We claim:

1. A 2-silacoumarane of Formula I

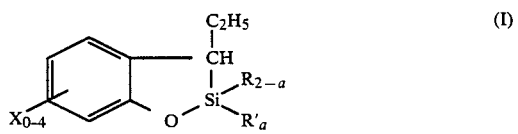

in which X represents halogen moieties and/or alkyl or fluorinated alkyl moieties with 1 to 4 carbon atoms, R' represents chlorine moieties or alkoxy moieties with 1 to 4 carbon atoms, R represents identical or different alkyl moieties with 1 to 4 carbon atoms and a=0 or 1 or 2.

2. A method for the preparation of cyclic phenol organosilane esters according to claim 1 comprising: esterifying an o-allylphenol of the general Formula III

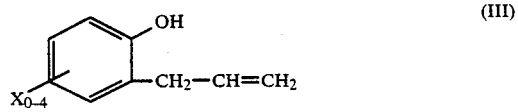

in which X has the same meaning as above, with a hydrogen chlorosilane of the general Formula IV

$HSiR_{2-a}Cl_{a+}$ (IV)

to the o-allylphenol silane monoester of Formula II; and subjecting the o-allylphenol silane monoester to cyclization in an inert diluent by catalytic hydrosilation.

3. The method of claim 2 further comprising esterifying the cyclized product.

4. The method of claim 2 wherein the esterification of the allylphenol with the hydrogen chlorosilane is performed with an excess of di- or trichlorosilanes.

5. The method of claim 2 wherein the esterification of the o-allylphenols is performed in the presence of inert diluents.

6. The method of claim 2 wherein the esterification of the o-allylphenol is performed by introducing it into the silane.

7. The method of claim 2 wherein the hydrogen chlorosilane is a hydrogen monochlorosilane and the esterification of the o-allylphenol is performed in the presence of an acid-binding substance.

8. The method of claim 2 wherein the cyclizing hydrosilation reaction is performed in the presence of a catalyst.

9. The method of claim 8 wherein the cyclizing hydrosilation reaction is performed at a temperature above 45° C. and the catalyst is a platinum or rhodium catalyst.

10. The method of claim 2 wherein the cyclizing hydrosilation reaction is performed without isolation of the o-allylphenol silane monoester following the esterification reaction of the o-allylphenol.

11. The method of claim 10 wherein the hydrosilation reaction is performed at temperatures above the boiling point of the hydrogen chlorosilane and excess hydrogen chlorosilane is continuously separated during the feed by a distillation apparatus.

12. The 2-silacoumarane of claim 1 which is Si-Si-dimethoxy-3-ethyl-2-silacoumarane.

13. The 2-silacoumarane of claim 1 which is Si-methyl-Si-methoxy-3-ethyl-2-silacoumarane.

14. The 2-silacoumarane of claim 1 which is Si-Si-dimethoxy-3-ethyl-4,6-dimethyl-5-chloro-2-silacoumarane.

15. The 2-silacoumarane of claim 1 which is Si-Si-diethoxy-3-ethyl-6-trifluoromethyl-2-silacoumarane.

16. The 2-silacoumarane of claim 1 which is Si-methyl-Si-chloro-3-ethyl-2-silacoumarane.

17. The 2-silacoumarane of claim 1 which is Si-Si-dimethyl-3-ethyl-4,5,6,7-tetrachloro-2-silacoumarane.

18. The 2-silacoumarane of claim 1 which is in mixture with an isomer thereof.

* * * * *

UNITED STATES PATENT AND TRADEMARK OFFICE
CERTIFICATE OF CORRECTION

PATENT NO. : 4,924,021

DATED : May 8, 1990

INVENTOR(S) : Hans-Joachim Kötzsch et al

It is certified that error appears in the above-identified patent and that said Letters Patent is hereby corrected as shown below:

Column 1, line 5, "1989" should read --1984--.

Column 4, line 7, the subscript "a-2" should read --2-a--.

Column 4, line 21, "a" should read --as--.

Column 6, line 56, "0.2 to 2" should read --0.2 to 12--.

Column 7, line 21, "yeas" should read --yeast--.

Column 10, line 8, "$D_4^{20}$ 4 1.1177" should read --$D_4^{20}$1.1177--.

Column 13, line 5, "curved" should read --cured--.

Column 13, line 6, "bending" should read --binding--.

Column 13, line 6, "20-2" should read --20-21--.

Column 13, line 43, the subscript "a+" should read --a+1--.

Signed and Sealed this

Sixth Day of April, 1993

*Attest:*

STEPHEN G. KUNIN

*Attesting Officer*     *Acting Commissioner of Patents and Trademarks*